United States Patent [19]

Otsuka

[11] Patent Number: 6,059,569
[45] Date of Patent: May 9, 2000

[54] APICAL POSITION DETECTION APPARATUS

[75] Inventor: Masahiro Otsuka, Kawasaki, Japan

[73] Assignee: Toei Electric Co., Ltd., Kanagawa, Japan

[21] Appl. No.: 09/190,829

[22] Filed: Nov. 12, 1998

[30] Foreign Application Priority Data

Aug. 24, 1998 [JP] Japan ................................. 10-237262

[51] Int. Cl.[7] .................................................. A61C 19/04
[52] U.S. Cl. .............................................. 433/72; 128/776
[58] Field of Search ................................ 433/72, 75, 27; 128/776

[56] References Cited

U.S. PATENT DOCUMENTS

| | | | |
|---|---|---|---|
| 5,017,134 | 5/1991 | Saito et al. ................................ | 433/72 |
| 5,096,419 | 3/1992 | Kobayashi et al. . | |
| 5,211,556 | 5/1993 | Kobayashi et al. . | |

FOREIGN PATENT DOCUMENTS

4126753C2 of 0000 Germany .
4139424C2 of 0000 Germany .
19854223 5/1999 Germany .

*Primary Examiner*—Nicholas D. Lucchesi
*Attorney, Agent, or Firm*—Laff, Whitesel & Saret, Ltd.; J. Warren Whitesel

[57] ABSTRACT

The present invention provides an apical position detection apparatus for accurately detecting the fact that a measuring electrode arrives at the apical position. The apparatus has a first current value measuring means for measuring a first frequency value by supplying a first frequency signal between the measuring electrode and the oral electrode, a second current value measuring means for measuring a second frequency value by supplying a second frequency signal between the measuring electrode and the oral electrode, arithmetic means for obtaining logarithmically converted calculation value by using a first measurement signal and a second measurement signal, and position signal formation means for obtaining an apical position detecting signal by addition or subtraction of the first measurement signal and the arithmetic value.

8 Claims, 8 Drawing Sheets

| A | B | C | D | E | F | G | H | I | J |
|---|---|---|---|---|---|---|---|---|---|
| COEFFI-CIENT | IMPEDANCE | MEASUREMENT CURRENT | | CURRENT RATIO | CURRENT CHANGE RATE | INCREASE | CORRECTED CURRENT CHANGE RATE | LOGARITHMIC CURRENT CHANGE RATE | CORRECTED LOGARITHMIC VALUE |
| K | Z1 | i1 | i2 | i2/i1 | \|i2−i1\|/i1 | | | | |
| 100 | 4549.0 | 18.02 | 39.27 | 2.179 | 29.474 | 0.00 | 62.2 | 29.39 | 72.2 |
| 90  | 4094.1 | 19.63 | 41.81 | 2.130 | 28.242 | 1.61 | 62.0 | 29.02 | 72.2 |
| 80  | 3639.2 | 21.56 | 44.70 | 2.074 | 26.839 | 3.54 | 61.8 | 28.58 | 72.2 |
| 70  | 3184.3 | 23.90 | 48.02 | 2.009 | 25.228 | 5.88 | 61.7 | 28.04 | 72.2 |
| 60  | 2729.4 | 26.81 | 51.87 | 1.934 | 23.359 | 8.79 | 61.9 | 27.37 | 72.3 |
| 50  | 2274.5 | 30.54 | 56.39 | 1.847 | 21.164 | 12.52 | 62.3 | 26.51 | 72.3 |
| 40  | 1819.6 | 35.47 | 61.78 | 1.742 | 18.549 | 17.45 | 63.3 | 25.37 | 72.3 |
| 30  | 1364.7 | 42.29 | 68.31 | 1.615 | 15.381 | 24.27 | 65.4 | 23.74 | 72.2 |
| 20  | 909.8  | 52.36 | 76.38 | 1.459 | 11.465 | 34.34 | 69.6 | 21.19 | 71.7 |
| 10  | 454.9  | 68.73 | 86.61 | 1.260 | 6.501  | 50.71 | 78.5 | 16.26 | 69.3 |
| %  | C1=0.05u Fr1=6.5K Z1=*K% | | | x COEFFI-CIENT | =\|i2−i1\|/i1 | =i1−(K=100) =i1−(CHANGE) | i1+F COLUMN *1.5 | 20log 10F COLUMN | C COLUMN ÷ I COLUMN *4.3/2 |

FIG. 6A  ROOT-TIP POSITION

FIG. 6B  BEFORE ROOT-TIP POSITION

FIG. 6C  OVER ROOT-TIP POSITION

FIG. 6D  ROOT CANAL ENTRANCE

APICAL POSITION DETECTION APPARATUS

BACKGROUND OF THE INVENTION

The present invention relates to an apical position detection apparatus for use in dental diagnosis and treatment.

In the dental treatment, there are some cases where dental pulp and nerve must be removed from a root canal. In these cases, the operator first measures the distance from a crown to an apical of the root (root tip). Thereafter, the dental pulp and nerve are removed by the measured distance from the root canal. To measure the distance, an apical position detection apparatus is used. The apical position detection apparatus detects the apical position by arranging an oral electrode in an oral cavity and a measuring electrode in a root canal, supplying an alternating current signal between the measuring electrode and the oral electrode, and detecting the apical position on the basis of the measurement signal obtained when the measuring electrode reaches the apical position.

The operator inserts the measuring electrode from the crown toward the apical and monitors whether a pointer of a display section indicates a predetermined position when the measuring electrode reaches the apical.

In the dental treatment, it is important to detect the apical position, accurately. In the case where the apical position is not determined accurately, the distance from the crown to the apical deviates from the real distance thereof. If the treatment is applied relying upon the measured distance (which deviates from the real distance), the pulp and nerve may remain within the root canal after the treatment. Otherwise, the apical may be destroyed during the treatment.

As described, it is important to detect the apical position, accurately. However, a conventionally used apical position detection apparatus is still insufficient in respect of accuracy.

BRIEF SUMMARY OF THE INVENTION

An object of the present invention is to provide an apical position detection apparatus capable of detecting the fact that the measuring electrode reaches the apical position, with high accuracy.

In the present invention, it is possible to simply display the movement of the measuring electrode until it reaches the apical position, thereby improving the operation manner for the user. More specifically, the present invention is directed to the apical position detection apparatus capable of displaying the pointer movement of the display section in the same manner as in the conventionally used apparatus which has been evaluated as a simple and adaptable means to practical dental examination operation.

To attain the aforementioned objects, the present invention employs a measurement principle based on a quite novel technical idea in an apical position detection apparatus for detecting the apical position. The apical position detection apparatus determines the apical position by arranging an oral electrode in an oral cavity and a measuring electrode in a root canal, supplying an alternating current signal between the measuring electrode and the oral electrode, and determining the apical position on the basis of the measurement signal obtained when the measuring electrode reaches the apical position.

To explain the principle more specifically, a first frequency signal is supplied between the measuring electrode and the oral electrode to obtain a first measurement signal. On the other hand, a second frequency signal is supplied between the measuring electrode and the oral electrode to obtain a second measurement signal. Then, logarithmically converted calculation value is obtained by using the first and second measurement values thus obtained. Then, the first measurement signal and the arithmetic values are subjected to arithmetic operation such as addition or subtraction, thereby obtaining the apical detecting signal.

The apical position is basically detected by the first measurement signal based on the first frequency in accordance with the aforementioned means. However, correction is usually made by the arithmetic value varying depending upon environmental factors. The arithmetic value used herein is a logarithmically converted value of the measurement signal. Due to the logarithmic nature, highly accurate arithmetic value is obtained. As a result, the apical position detecting signal representing that the measuring electrode reaches the apical position can be obtained with high accuracy.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Now, embodiments of the present invention will be explained with reference to the accompanying drawings.

Figure 1:
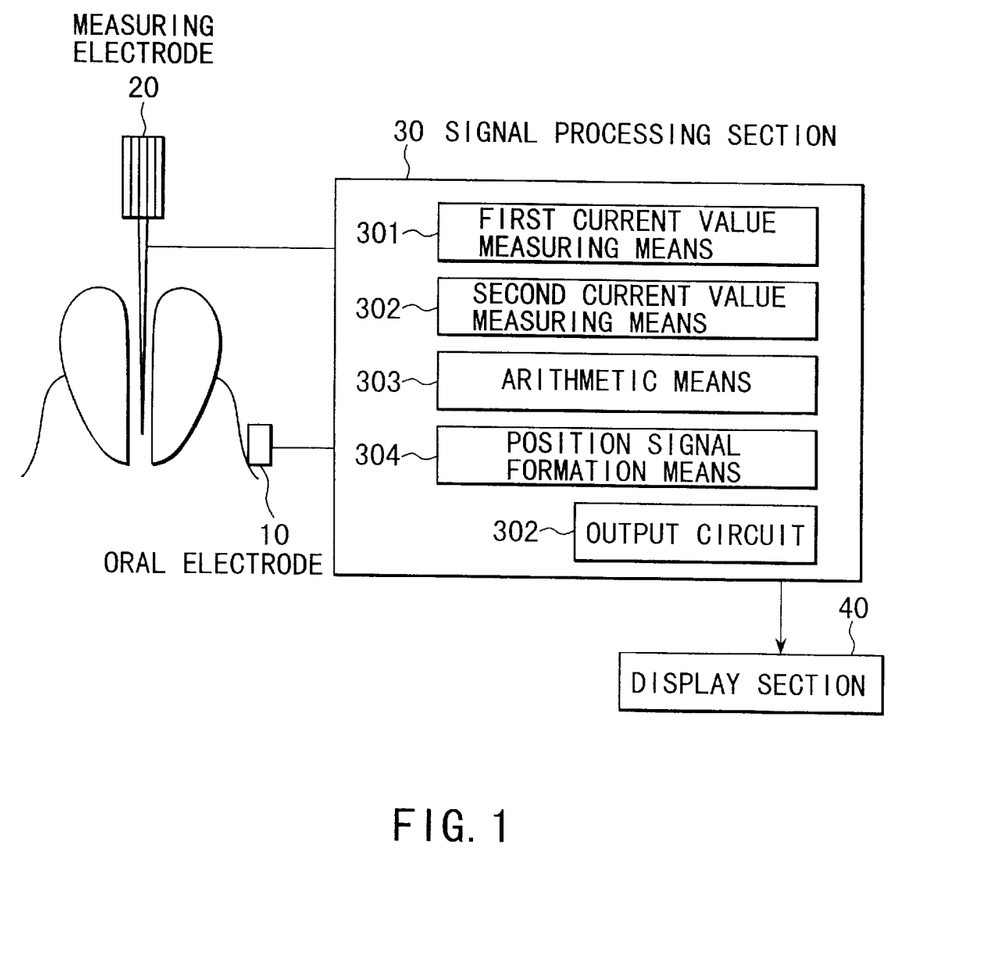
FIG. 1 is a view showing a basic structure of the apical position detection apparatus of the present invention.

Referring to the block diagram of FIG. 1, the entire structure of the apical position detection apparatus will be first explained. The apparatus has an oral electrode 10 to be set in touch with the gums and a pin-shape measuring electrode 20 to be inserted into the root canal. The signal processing section 30 includes a first current value measuring means 301, a second current value measuring means 302, an arithmetic means 303 and a position signal formation means 304. The first current value measuring means 301 is responsible for measuring a first current value by supplying a first frequency signal between the measuring electrode 20 and the oral electrode 10. The second current value measuring means 302 is responsible for measuring a second current value by supplying a second frequency signal between the measuring electrode 20 and the oral electrode 10. The arithmetic means 303 plays a role in obtaining an arithmetic value by using the first current value (obtained by the first current value measuring means 301) and the second current value (obtained by the second current value measuring means 302). The position signal formation means 304 plays a part of obtaining an apical position detecting signal through arithmetic operation (addition or subtraction) using the first current value and the arithmetic value. The apical position detecting signal obtained by the position signal formation means 304 is sent to the display section 40 by way of an output circuit 305 for display.

Figure 2:
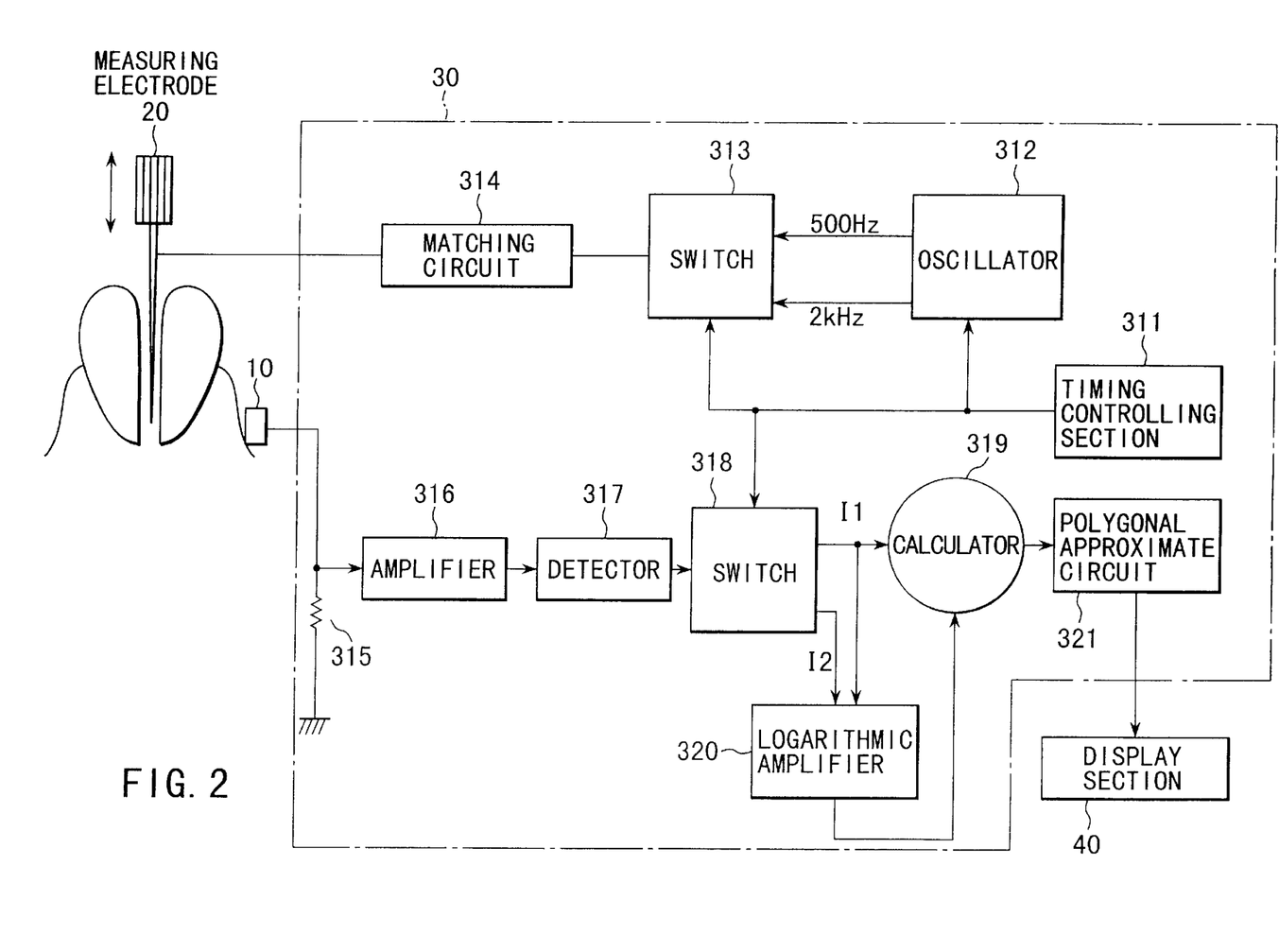
FIG. 2 is a detailed circuit diagram of the apparatus of FIG. 1.

FIG. 2 is a block diagram showing a circuit of the signal processing section 30 more precisely. A timing control section 311 controls the entire operation of the apparatus including switching of all signal processing pathways and receipt of operation signal. An oscillator 312 generates oscillation signals of 500 Hz (first frequency) and 2 kHz (second frequency). Either 500 Hz or 2 kHz oscillation signal is selected by the operation of a switch 313 and supplied to a measuring electrode 20 by way of a matching circuit 314.

Current defined by impedance (described later) flows between the measuring electrode 20 and the oral electrode 10. The oral electrode 10 is not only grounded through a detection resistance 315 but also connected to an input terminal of an amplifier 316. The AC signal current amplified by the amplifier 316 is converted into a direct current through the detector 317 and supplied to an input terminal of a switch 18. The operation of the switch 318 is controlled on the basis of a control signal sent from the timing control section 311. When the 500 Hz signal is employed, a detecting current $i1$ is supplied to an arithmetic unit 319 and a logarithmic amplifier 320, whereas the 2 kHz signal is employed, a detection current $i2$ is supplied only to the logarithmic amplifier 320.

In the logarithmic amplifier 320, the following calculation is performed to obtain an arithmetic value G:

$$20 \log_{10} [(i2-i1)/i1]$$

The arithmetic value G is input into the arithmetic unit 319. In the arithmetic unit 319, the following calculation is performed to obtain an apical position detecting signal X:

$$X = i1(\text{first current value}) + G(\text{arithmetic value})$$

The apical position detecting signal X is introduced into the display section 40 by way of a polygonal approximate circuit.

In the signal processing circuit 30, the first current value measuring means 301 is constituted of a passage starting from the oscillator 312, switch 313, matching circuit 314, measuring electrode 20, oral electrode 10, detection resistance 315, amplifier 316, detector 317, to the switch 318 when 500 Hz signal is output. Similarly, the second current value measuring means 302 is constituted of the passage starting from the oscillator 312, switch 313, matching circuit 314, measuring electrode 20, oral electrode 10, detection resistance 315, amplifier 316, detector 317, to switch 318, when 2 kHz signal is output. Furthermore, the logarithmic amplifier 320 corresponds to the arithmetic means 303. The arithmetic unit 319 corresponds to the position signal formation means 304.

In the above, we have explained that two measuring means are present respectively as the first and second current value measuring means. In practice, however, substantially one measuring means may be good enough if one measuring means is used in time-sharing manner. As a result, the signal processing section 30 may be formed of a microprocessor storing software.

Now, we will explain the principle how to detect the apical position by the apical position detection apparatus.

Figure 3A:
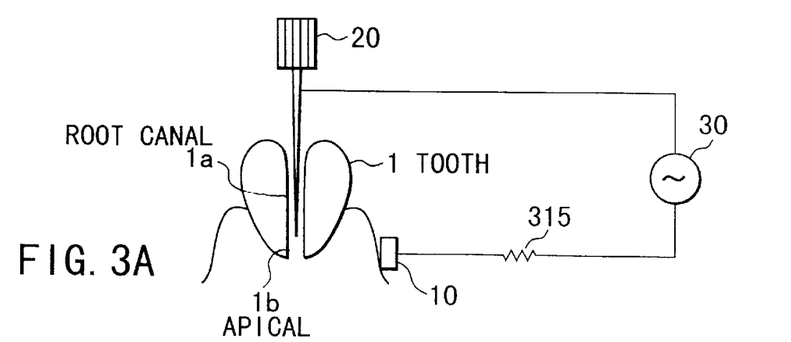
FIGS. 3A to 3C are equivalent circuits for use in explaining the principal of the apical detection according to the present invention.
Figure 3B:
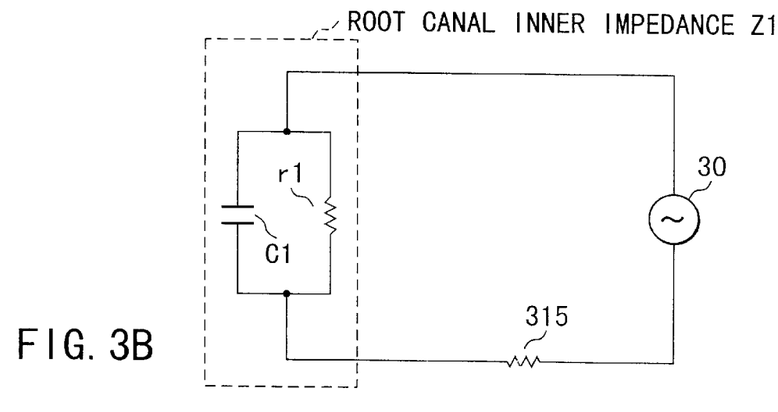
Figure 3C:
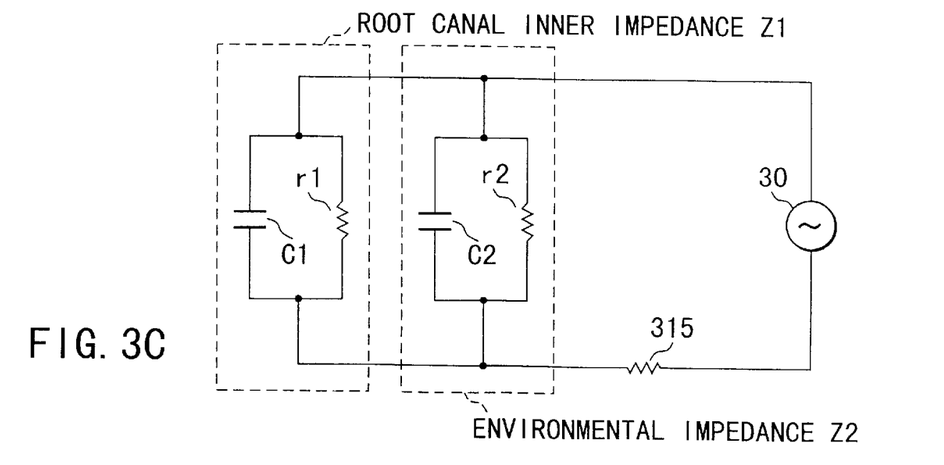

FIG. 3A schematically shows a basic structure of the apical position detection apparatus. FIG. 3B shows a circuit equivalent to a circuit formed in the detecting apparatus applied to a dry-state root canal. FIG. 3C shows a circuit equivalent to a circuit formed in the detecting apparatus applied to the root canal in which medicinal liquids and blood are present at the apical position thereof.

Figure 4:
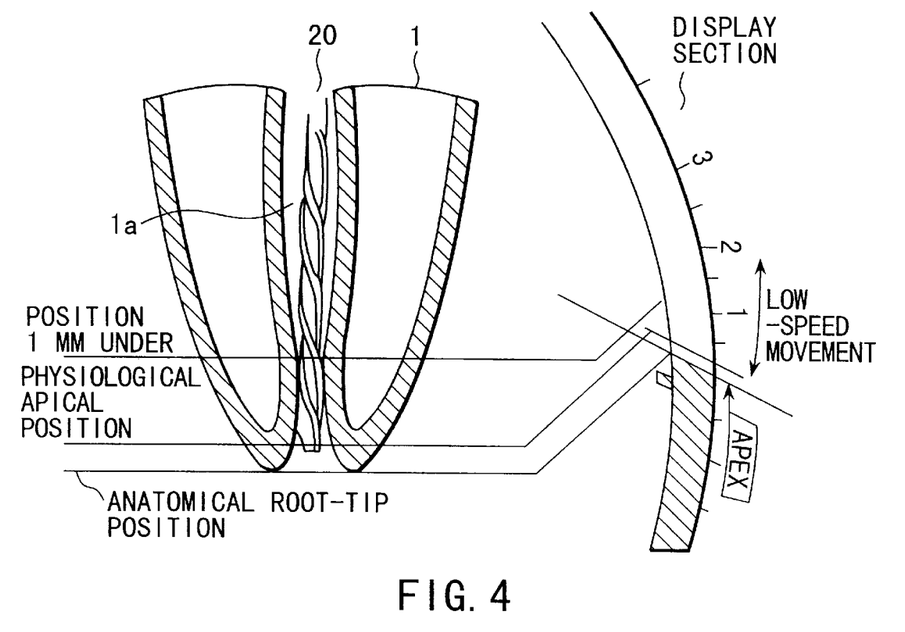
FIG. 4 is a profile of a display section when the measuring electrode reaches the apical position.

As shown in FIG. 3A, the measuring electrode 20 is inserted into a root canal $1a$ of a tooth 1. As a leading edge of the measuring electrode 20 approaches near an apical $1b$, a pointer 41 of the display section 40 moves and indicates a predetermined position, APEX, as shown in FIG. 4. This is because the impedance between the electrodes decreases as the measuring electrode 20 proceeds deep inside the root canal and presents a predetermined value when the leading edge of the measuring electrode reaches the apical. To explain more specifically, the phenomenon occurs by use of the fact that the current value between the apical mucous membrane and oral membrane is constant since the electrical resistance between them is low and constant.

As shown in FIG. 3B, when the root canal is in a dry state, the impedance between the measuring electrode 20 and the oral electrode 10 can be replaced by impedance within the root canal (hereinafter referred to as "root canal inner impedance Z1") obtained in a circuit comprising a resistance r1 and a condenser c1 connected in parallel. In this case, when the measurement signal of 500 Hz is influenced by the root canal inner impedance Z1, the detection current $i1$ can be expressed by the following equation:

$$i1 \text{ (ampere)} = V/(R+Z1)$$

where V is a measured voltage and R is a value of detection resistance 315.

If the current value $i1$ reaches a predetermined value while inserting the measuring electrode 20, it can be determined that the leading edge of the measuring electrode 20 arrives at the apical.

However, actually environment factors such as medicinal liquids and blood are present in the root canal in various amounts. Therefore, the current values obtained in the vicinity of the apical and right at the apical position inevitably include detection error in the imaginary circuit shown in FIG. 3B. To cancel the error, it is necessary to know an accurate amount of the error.

Then, the present inventors pay attention to the fact that there is an impedance $Z_2$ varying depending upon environmental changes (hereinafter, referred to as "environmental impedance $Z_2$"), as shown in FIG. 3C, and the environmental impedance $Z_2$ causes the error particularly in the vicinity of the apical position. When the environmental impedance $Z_2$ is connected to the root canal inner impedance $Z_1$ in parallel, synthetic impedance decreases. As a result, the measurement current value sometimes increases although the leading edge of the measuring electrode 20 has not yet reach the apical position, causing a phenomenon that the measurement current value reaches the predetermined value before the measuring electrode reaches the apical.

Therefore, if the error (given by arithmetic value) is subtracted from the measurement current value, the correct (real) current value can be obtained.

Next, we will explain a method how to obtain the arithmetic value.

To obtain the arithmetic value, it is necessary to know the change in measurement current depending upon the environment change since the measurement current deviates from the real value if the medicinal liquids and blood are present when the measuring electrode reaches the apical. To determine the change in measurement current, current is measured by using the 500 Hz signal and the 2000 Hz signal, which is 4 times as lager as 500 Hz. Then, we checked how to change the impedance depending upon environmental change in the circuit shown in FIG. 3C.

Figure 5A:
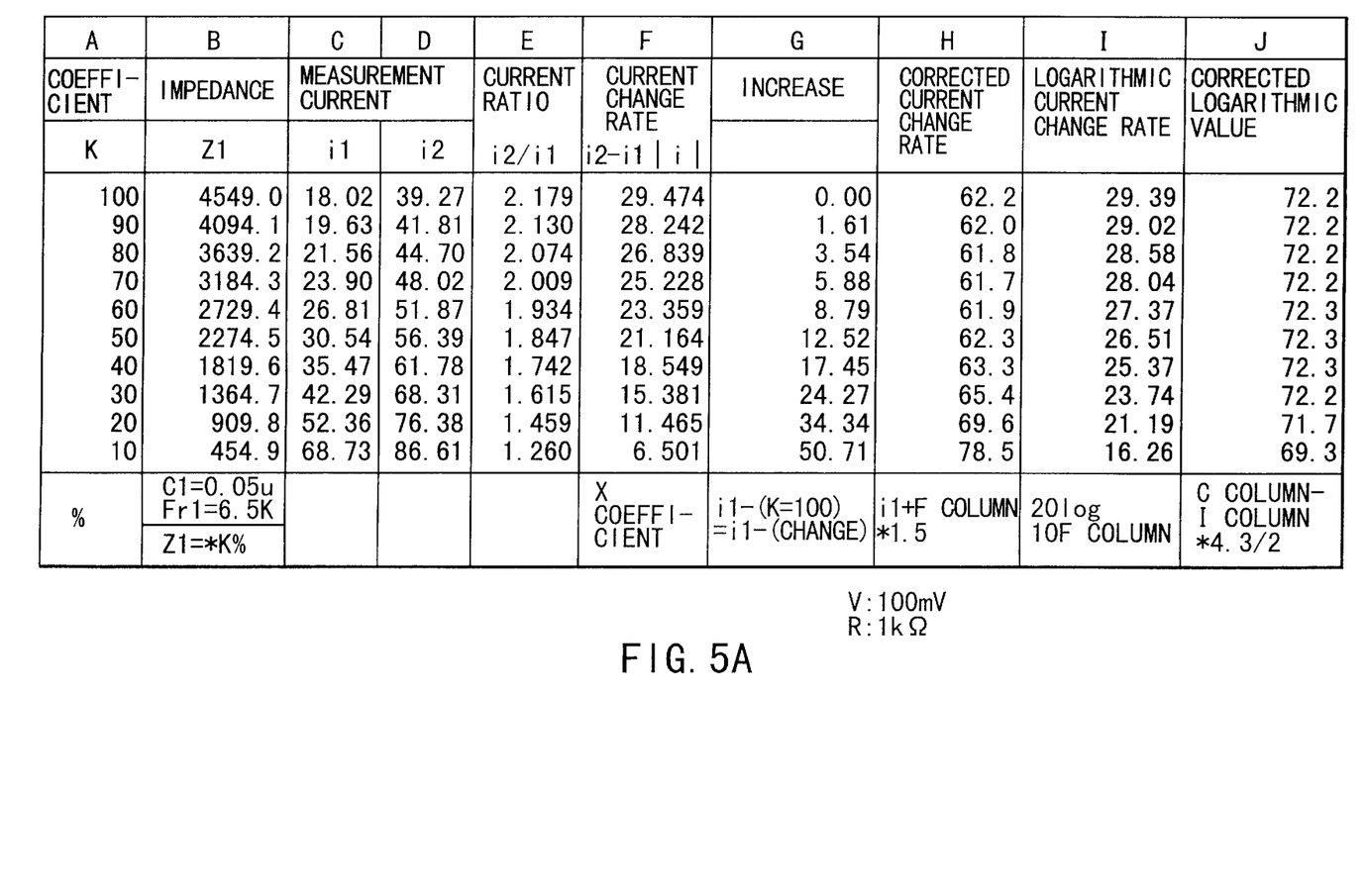
FIG. 5A is a table showing measurement currents and arithmetic values under various environmental factors when the measuring electrode reaches the apical position in the apparatus of the present invention.

The resultant data are shown in FIG. 5A. We will explain the columns sequentially from the left column A. The data of each column may be used by multiplying a constant in some cases. The constant is used to match an input level to an output level on the circuit, or to express the characteristics on a graph. Therefore, a fundamental arithmetic equation will not be affected by the use of the constant.

In the circuit shown in FIG. 3C, the elements constituting root canal inner impedance $Z_1$ are defined as follows: $c_1 = 0.05$ µF, $r_1 = 6.5$K. Assuming that the impedance $Z_1$ measured under the 500 Hz signal supply varies from, for example, 100%, 90%, 80% ... 10%, as shown in column A, the value in the column B changes from 4549.0, 4094.1, 3639.2, ... to 454.9. These changes are caused by environmental impedance $Z_2$.

As the impedance $Z_1$ changes as described above, the measurement current $i_1$ measured under the 500 Hz signal supply varies as shown in column C and the measurement current $i_2$ measured under the 2000 kHz signal supply varies as shown in column D. A current ratio ($i_2/i_1$) and a current change rate ($i_2-i_1$)/$i_1$ are shown based upon the measurement currents. The column G titled "increase", shows an increase in the measurement current $i_1$, which varies depending upon the change in impedance $Z_1$. The "corrected current change rate" shown in the column H is obtained by multiplying the current change rate by 1.5 and adding the measurement current $i_1$ to the product obtained. The value 1.5 is used as the coefficient to amplify the range of the current change rate. A logarithmic current change rate is obtained by using the following logarithmic equation which is a feature of the present invention:

$$G = 20 \log_{10} [(i2-i1)/i1]$$

Furthermore, the detection value is expressed by the following equation:

$$X = i1 + G$$

In this case, the value obtained by multiplying G by a constant 4.3, added with $i_1$, and divided by a constant 2, is used.

Figure 5B:
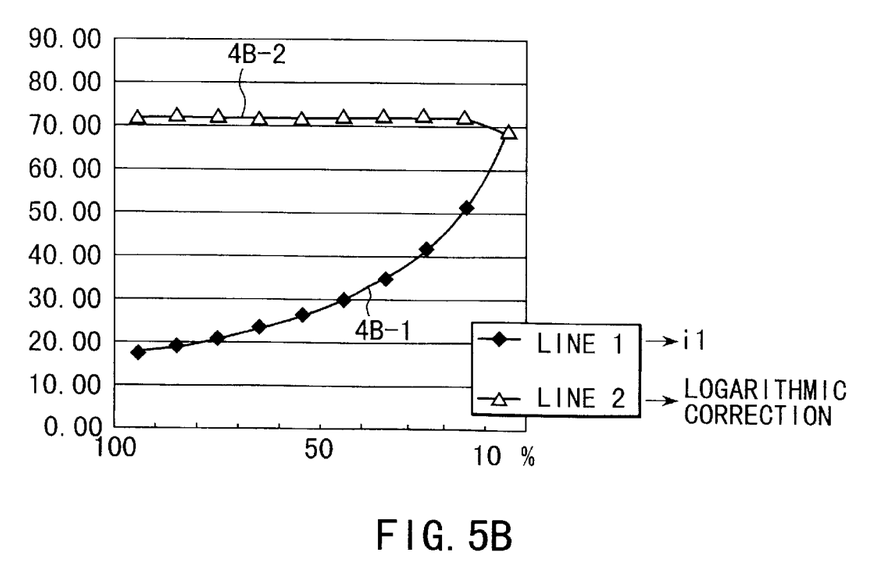
FIG. 5B is a graph showing column C and column J of FIG. 5A.

In FIG. 5B, the magnitude of environmental change is plotted on the abscissa and the current value listed in the table of FIG. 5A is plotted on the ordinate. The curve 4B-1 indicates the profile of the column C.

In the present invention, current $i_1$ is corrected by using the logarithmic current change rate. That is, the correction is made in accordance with arithmetic equation by employing the value G mentioned above:

$$X = i1 + G$$

The value G draws a curved line having opposite characteristics of the curved line 4B-1 if an appropriate constant is multiplied. Therefore, as the result of the arithmetic operation of $X = i1 + G$, a constant output of the apical position detecting signal can be obtained regardless of the environmental change. In other words, it is possible to accurately indicate that the measuring electrode has arrived at the apical position without error. It is the curved line 4B-2 that express the profile of the output of the apical position detecting signal.

According to the present invention, it is possible to output the detection signal when the measuring electrode reaches at the apical position without error due to the medicinal liquids and blood. More specifically, the predetermined current value obtained when the apical position is accurately detected can be obtained.

Now, we will explain the reason why 500 Hz and 2000 Hz signals are employed in the present invention.

Figure 6A:
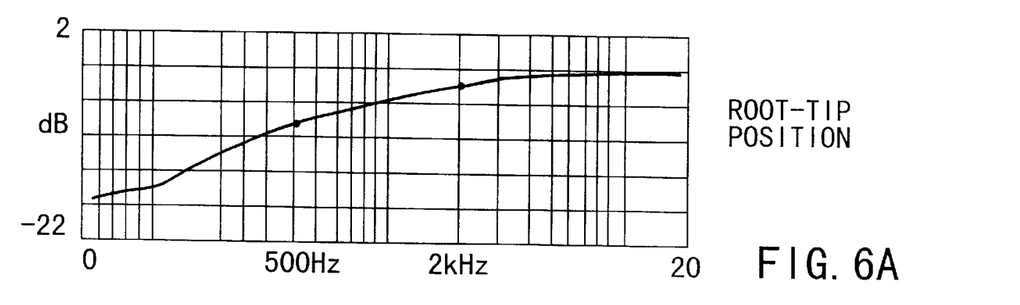
FIGS. 6A to 6D are graphs showing levels of 500 Hz and 2 kHz signals measured at various positions at which the measuring electrode is located.

FIGS. 6A to 6D show frequency characteristics obtained under various environmental conditions associated with the circuit shown in FIG. 3C. FIG. 6A shows frequency band characteristics when the measuring electrode reaches the apical position with saline which has been injected in the root canal. In this case, the output level of 500 Hz clearly differs from that of 2000 Hz. This is because the aforementioned two signals are selected from the area in which the band characteristics linearly change. It is important to use such a region. This is because if the difference in level is not obtained between the two signals, the product of the following logarithmic equation cannot be obtained:

$$G = 20 \log_{10} [(i2-i1)/i]$$

Figure 6B:
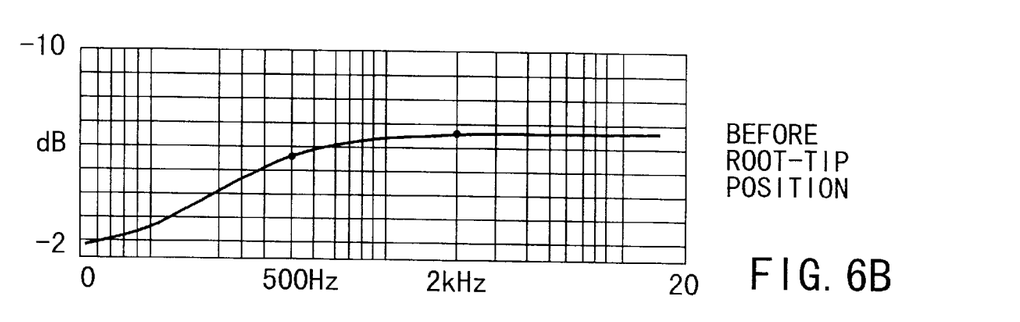
Figure 6C:
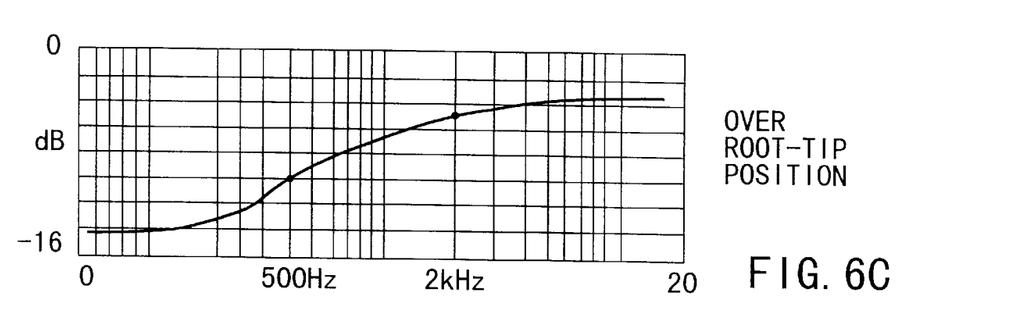
Figure 6D:
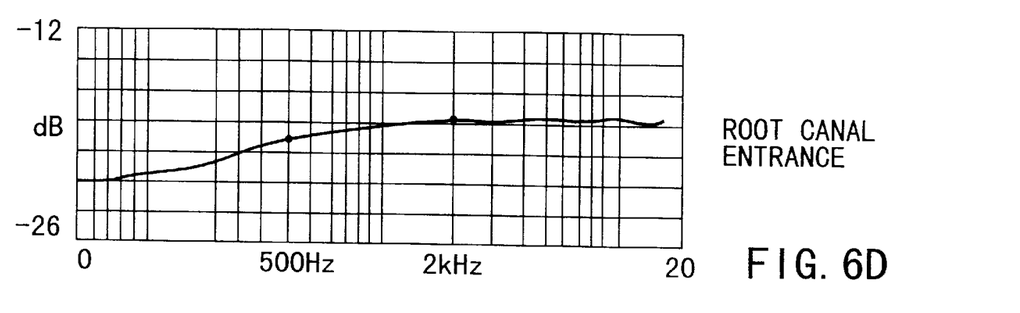

Similarly, frequency characteristics determined just before the measuring electrode reaches the apical position are shown in FIG. 6B. In this case, since the output level of 500 Hz signal clearly differs from that of 2000 Hz, logarithmic calculation can be performed sufficiently to obtain the product. FIG. 6C shows the case where the measuring electrode overextends the apical position. FIG. 6D shows the frequency characteristics when the measuring electrode is positioned at an entrance of the root canal. In this case, the difference in output level between the 500 Hz signal and the 2000 Hz signal is relatively low. In other words, environmental impedance $Z_2$ has a little effect on the equivalent circuit shown in FIG. 3C. This means that the environmental impedance $Z_2$ particularly brings a large effect on the portion close to the apical position.

As described, the present invention is intended to detect the apical position by use of frequencies within the area in which the band characteristics form the linear line as the measurement signals.

Furthermore, in the apical position detection apparatus of the present invention, the polygonal approximate circuit 321 is provided. By virtue of the presence of the polygonal approximate circuit 321, the measuring electrode can be operated easily when the measuring electrode approaches the apical position. More specifically, as shown in FIG. 4, when the measuring electrode arrives at the apical position, the pointer of the display section points out the predetermined position (APEX) in the same manner as in the conventionally-used detecting apparatus employing a single frequency. Therefore, the operator can insert the measuring electrode carefully in the same manner as in the conventionally-used apparatus. At the same time, it is possible to prevent a rush and rough operation so as not to break the apical.

Figure 7A:
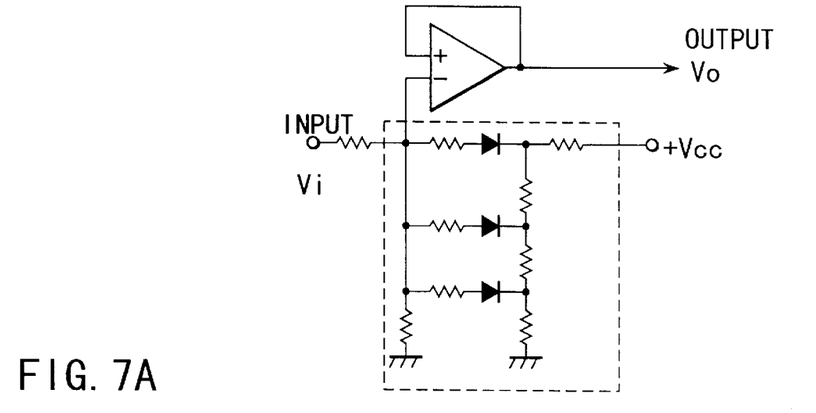
FIG. 7A is a polygonal approximate circuit.
Figure 7B:
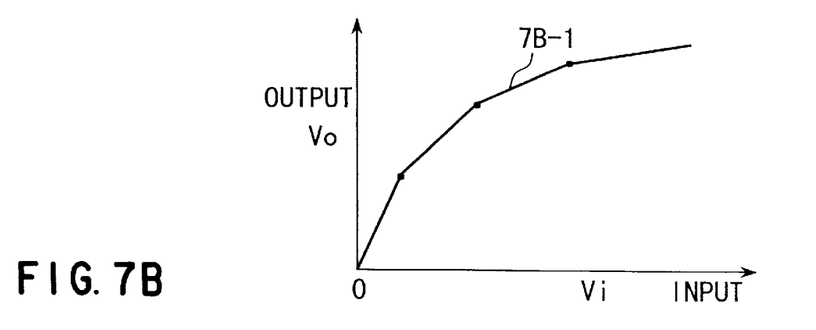
FIG. 7B shows characteristics of the circuit shown in FIG. 7A.

FIGS. 7A and 7B show the polygonal approximate circuit 321 and the characteristics thereof, respectively. The polygonal approximate circuit 321 is constituted of an arithmetic amplifier 30 and a diode clamp circuit 31 formed of the plurality of stages. The polygonal approximate circuit 321 is characterized in that the change rate of the output voltage Vo becomes smaller as the input voltage Vi becomes larger. Because of the functional characteristics of the circuit, the pointer of the display section moves in its entirety during the period that the leading edge of the measuring electrode moves from the crown to the apical. Therefore, the operator can handle the measuring electrode easily while monitoring the pointer.

Now, we will add further explanation to FIG. 7B. The curved line 7B-1 shows the change in output voltage VO when the input voltage Vi to the polygonal approximate circuit 321 changes linearly. The curved line 7B-1 may draw a parabola curve or a curve changing like a step function response (for example, saturation curve) of the CR circuit. The shape of the curve may be selected arbitrarily. Any shaped curve can be employed as long as the pointer of the display section can be moved in the same manner as in the conventionally used one by the output of the arithmetic unit 319.

To prevent the output from the arithmetic unit 319 from changing rapidly just before the apical, it may be possible to set the characteristics of the output from the arithmetic unit 319 so as to change linearly or almost linearly. However, the linear change is too rapid for the operator to manipulate the measuring electrode easily, in consideration of the practical treatment. This is because if the linear change is employed, the operator must operate the measuring electrode more carefully when the electrode reaches 1 or 2 mm before the apical.

In the present invention, it is rather important that movement of the measuring electrode from the crown to the apical can be visually monitored. Then, the polygonal approximate circuit 321 is designed in such a way that the pointer of the display section moves in the same manner as in that of the conventionally-used apparatus.

For the reason mentioned above, the input and output characteristics of the polygonal approximate circuit 321 are set in the same manner as shown in the step function response (for example, a saturation curve or a parabola curve) of the CR circuit.

Figure 8:
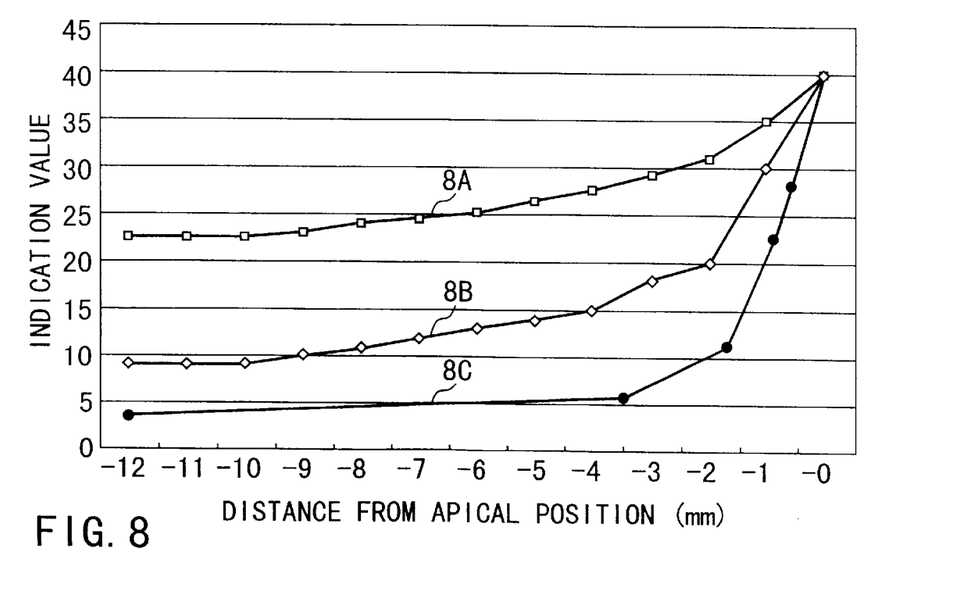
FIG. 8 is a graph showing the pointer movement on the display (plotted on the ordinate) and shows moving distance of the measuring electrode (plotted on the abscissa), and exhibiting characteristics of the input signal introduced into the polygonal approximate circuit from an arithmetic unit by comparing the pointer movement of the display section of the present invention and the pointer movement of a econventionally-used apparatus.

FIG. 8 shows the relationship between the movement of the pointer of the display section 40 (plotted on the ordinate) and the moving position of the measuring electrode (reamer) 20 (plotted on the abscissa). Point "0" on the abscissa represents the apical position. Point "40" on the ordinate is the predetermined moving position of the pointer when the measuring electrode reaches the apical.

The curved line 8A indicates the profile of the pointer movement when the apical position is detected by use of the conventional measuring apparatus (for example, ENDODONTIC METER-SII) employing a single frequency. The curved line 8B shows the profile of the pointer movement of the display section 40 in the detecting apparatus of the present invention. FIG. 8C shows the characteristics of the input signal into the polygonal approximate circuit 321.

As the leading edge of the measuring electrode 20 approaches the apical "0" from the position 12 mm away from the apical, the pointer of the display section 40 approaches to the graduation "40" in the same behavior as shown in the conventionally-used apparatus.

The display pointer is designed so as to behave as shown by the curve 8B in the present invention. This is because the present inventor found that the behavior (curve 8A) of the pointer of the conventionally used display section is suitable for a practical operation performed during the dental diagnostic examination. If the moving behavior of the display pointer is set more similar to those of the curve 8A, it is possible to observe the movement of the pointer in the display section 40 of the present invention more easily. In addition, it is advantageous for the operator to handle such an apparatus similar to the conventional one since the operator has been accustomed to the operation manner for the conventional detecting apparatus.

Note that the present invention is not limited to the aforementioned embodiment.

In the embodiment, current flowing through the detection resistance is measured and then X=i1+G is obtained on the basis of the measurement signal. However, the voltage across the detection resistance may be used as the measurement signal. The measurement signal thus obtained may be subjected to the arithmetic operation to obtain the apical position detection signal.

Figure 9:
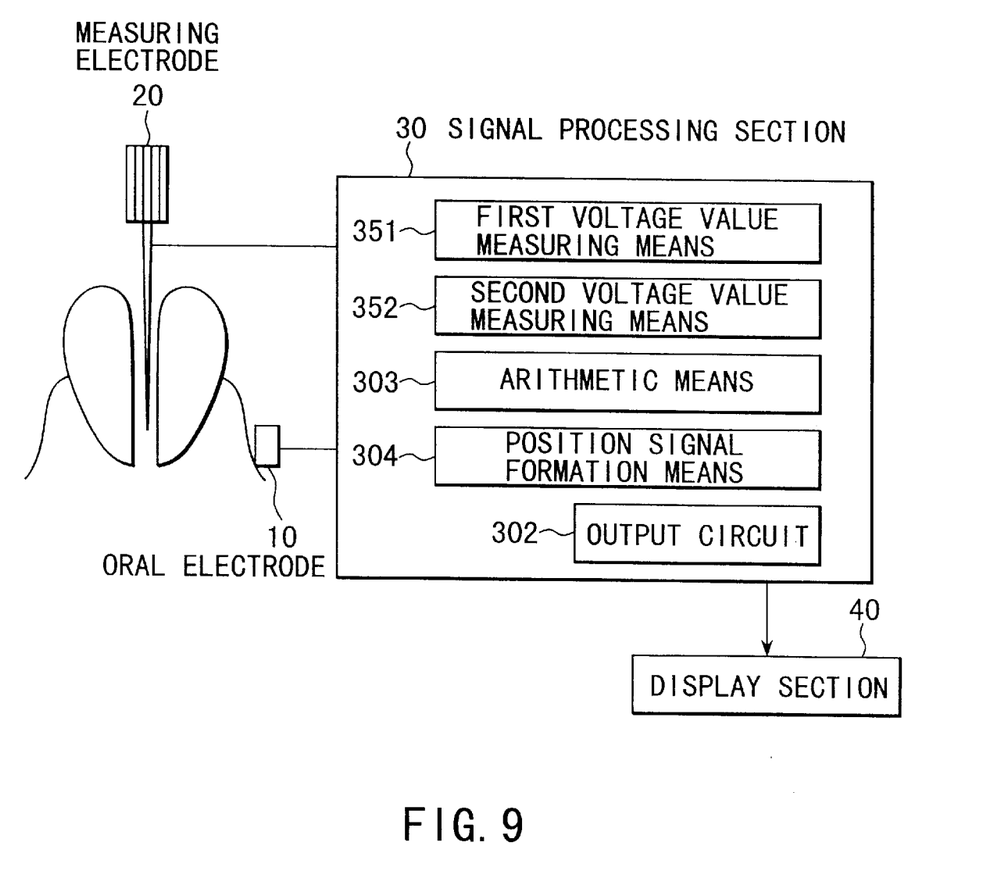
FIG. 9 is an apparatus according to another embodiment of the present invention.

The apical position detection apparatus may have the signal processing section 30 as shown in FIG. 9. That is, the signal processing section 30 has a first voltage measuring means 351 and a second voltage measuring means 352 as the measuring means. The detection signal may be obtained in the same processing manner from the voltage value by use of the arithmetic means as in the aforementioned embodiments. Like reference numerals are used for other portions to designate like structural elements corresponding to those in the previous embodiment and any further explanation is omitted for brevity's sake.

The present invention is not limited to the aforementioned embodiment. A voice apical position notification means may be provided in the apparatus. The voice apical position notification means gives sound intermittently when the measuring electrode approaches the apical position and gives a continuous sound when the tip position is detected. As the signal to be used in the sound position notification means, either output from the arithmetic unit 319 and output from the polygonal approximate circuit 321 may be used.

According to the present invention explained in the foregoing, it is possible to detect the fact that the measuring electrode reaches the root top portion, with high accuracy. In addition, the profile that the leading edge of the measuring electrode approaches the apical portion, is visually and simply displayed. As a result, the operation manner for the apical position detection apparatus can be improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apical position detection apparatus for detecting an apical position by arranging an oral electrode in an oral cavity and a measuring electrode in a root canal, supplying an alternating current signal between the measuring electrode and the oral electrode, and detecting the apical position on the basis of the measurement signal obtained when the measuring electrode reaches the apical position, which comprises:

first measuring means for obtaining a first measurement signal by supplying a first frequency signal between the measuring electrode and the oral electrode;

second measuring means for obtaining a second measurement signal by supplying a second frequency signal between the measuring electrode and the oral electrode;

arithmetic means for obtaining a logarithmically converted calculation value by using the first measurement signal obtained by the first measuring means and a second measurement signal obtained by the second measuring means; and position signal formation means for obtaining an apical position detecting signal by addition or subtraction of the first measurement signal and the arithmetic value.

2. The apical position detection apparatus according to claim 1, wherein said first and second measurement signals are signals indicating current values.

3. The apical position detection apparatus according to claim 2, wherein an arithmetic value G is obtained by said arithmetic means in accordance with the following equation:

$$G = 20 \log_{10} [(i2-i1)/i1]$$

where $i1$ is the first current value and $i2$ is the second current value.

4. The apical position detection apparatus according to claim 3, wherein the apical position detecting signal X is obtained by said position signal formation means in accordance with the following equation:

$$X = i1 + G.$$

5. The apical position detection apparatus according to claim 3, wherein a polygonal approximate circuit is arranged between the position signal formation means and the display section, for converting a change in characteristics of the apical position detecting signal.

6. The apical position detection apparatus according to claim 1, wherein said first frequency is one in the vicinity of 500 Hz and said second frequency is one in the vicinity of 2000 Hz.

7. The apical position detection apparatus according to claim 1, wherein level of the second frequency is virtually four times as large as that of the first frequency.

8. The apical position detection apparatus according to claim 1, wherein two frequencies are selected, as said first and second frequencies, from a region in which frequency characteristics of the equivalent circuit formed between the oral electrode and the measuring electrode, show virtually a lineal line.

* * * * *